United States Patent [19]

Dumas et al.

[11] Patent Number: 4,967,187

[45] Date of Patent: Oct. 30, 1990

[54] METHOD AND APPARATUS FOR PARTICLE CONCENTRATION DETECTION USING A CLOUD CHAMBER

[75] Inventors: Jerome E. Dumas, Johns Island; Eric W. Harris, Jr., Moncks Corner; John G. MacDougal, Charleston, all of S.C.

[73] Assignee: Research Equipment Corporation, North Charleston, S.C.

[21] Appl. No.: 352,149

[22] Filed: May 15, 1989

[51] Int. Cl.⁵ .................... G08B 21/00; G08B 17/10
[52] U.S. Cl. .................................. 340/628; 340/627;
364/200; 356/37; 356/437; 356/438; 356/439;
73/863.01; 73/863.23; 250/335; 250/573
[58] Field of Search .................. 340/627, 507, 628;
250/335, 573; 356/437, 438, 439, 37; 73/863.01,
863.23; 364/200

[56] References Cited

U.S. PATENT DOCUMENTS

| | | | |
|---|---|---|---|
| 3,654,439 | 4/1972 | Estelle | 340/863.23 |
| 3,678,487 | 7/1972 | Ludewig, Jr. | 340/307 |
| 3,800,288 | 3/1974 | Russell | 364/200 |
| 4,764,758 | 8/1988 | Skala | 340/627 |
| 4,786,472 | 11/1988 | McConnell | 73/863.23 |

Primary Examiner—Joseph A. Orsino
Assistant Examiner—Kinfe-Michael Negash
Attorney, Agent, or Firm—Collard, Roe & Galgano

[57] ABSTRACT

Method and apparatus for sampling the gaseous medium of a zone or area to determine the concentration, or changes in concentration, of submicron particles suspended in the gaseous medium of that area or zone using an elongated cloud chamber. A light source and a phototransistor are disposed in the cloud chamber and spaced apart so as to be electronically responsive to varying levels of light. A microprocessor is connected to a programmable memory EPROM and has pre-programmed data instructions on particle concentration levels. The EPROM sequences the microprocessor to operate the valves that sequentially sample the gaseous medium in the cloud chamber, and opens the exhaust valve in the cloud chamber to create a condition of reduced gas pressure therein. The sample of gaseous medium containing submicron particles then precipitates or condenses a portion of the cloud in the chamber in proportion to the concentration of the particles. The phototransistor measures the change in light intensity due to the concentration of the particles. A data storage device records each of the particle concentration levels sensed and measured in the zone so dangerous levels of gas concentrations can be detected in the area or zone being treated.

20 Claims, 3 Drawing Sheets

METHOD AND APPARATUS FOR PARTICLE CONCENTRATION DETECTION USING A CLOUD CHAMBER

This invention relates to a particle monitor for measuring the concentration of submicron size particles in the air by means of a cloud chamber, and providing signals when the population density of the particles increases above a predetermined and preset levels.

BACKGROUND OF THE INVENTION

In different environments there is always an accumulation of particles of various sizes. By monitoring the concentration of particles within a narrow size range, the presence of a fire, even in its earliest stages, within the monitored space may be detected.

There are a number of fire detection devices that are used in both the home and industry that rely upon the accumulation of micron-size particles that can be sensed either by a photo optical or neutron detection device. In more sophisticated devices used in industry, air sampling actually takes place on a continuous basis wherein samples of air from the area being measured are compared with uncontaminated air to obtain a measure of the contamination of the zone. Such a device is shown in the Troup et al. Pat. No. 4,543,815. In other devices, corona-type ionizers are used to charge airborne particulate matter so that these particles can be detected electrically to sense the concentration of the particles. Such a device is described in U.S. Pat. No. 4,312,180.

FIELD OF INVENTION

There have also been developed particle detectors using radioactive materials, whereby the particles are charged by passing them through a unipolar ion cloud that is generated by a radioactive source so that with suitably charged electrodes the concentration of the particles can be detected. Such devices are described in U.S. Pat. No. 4,053,776 and U.S. Pat. No. 3,521,263.

BACKGROUND PROBLEM

More recently, there have been several particle detectors developed using a condensation nuclei monitor, or cloud chamber, in combination with a photo detector to detect an actual fire and can't tell if gas is dangerous or not. The discovery of the cloud chamber took place in 1911 by a British physicist, C. T. R. Wilson. Wilson noted that ionized gas molecules act as "seeds" around which water vapor in a cold-saturated atmosphere can condense into droplets of water by creating a chamber filled with cool, moist air. Wilson found that alpha particles or other radioactive particles capable of causing ionization of gas pass through the vapor-filled chamber and leave behind a trail of condensed water droplets in their wake seeded by the gas ions that they have created along the way. These long, thin streaks of fog within the cloud chamber could easily be illuminated by side lighting and photographed or detected through a transparent wall of the chamber. In U.S. Pat. No. 2,676,266 and U.S. Pat. No. 2,977,476 diffusion cloud chambers were disclosed for observing the cloud trails created when ionizing particles passed through the chambers. Cloud chambers, or condensation nuclei monitors, were then incorporated into devices for sampling and monitoring the air in different zones to detect the presence of fire. Such devices are shown in U.S. Pat. No. 3,667,488 and U.S. Pat. No. 3,757,583. In these prior art devices, one of four or more zones is monitored once every 15 seconds, and, by the use of a self-adjusting type cloud chamber coupled to a photo cell detector, any short-term changes in light level of a light beam directed upon the photo cell provides an indication of the particle concentration in that zone.

The prior art devices using cloud chamber detectors suffer from the disadvantages of being slow in their sampling rates of the air in any particular zone, and therefore lack sensitivity and the capability of an early detection of a dangerous particle concentration. Moreover, with respect to other types of gas detectors, the present invention measures the density of the vapor cloud, which depends upon the number of submicron particles, and not their size. Thus the present invention can be reliably used in "dirty" atmospheres where ionization or smoke detectors are useless. The improved sensitivity and quick sampling rates of the present invention allow the present invention to detect a slow or sudden increase the concentration of submicron particles which often occurs just prior to the start of combustion. In most cases, this permits the present invention to provide sufficient time for preventive action to take place after the alarm is given, or to provide an earlier warning than any other prior art device.

SUMMARY OF THE INVENTION

The present invention provides a method and apparatus for rapidly and continuously measuring the population density or concentration of submicron-sized particles in the air. Under normal conditions, a zone can contain thousands of particles per cubic centimeter. As a material in the protected space or zone is heated, it reaches the temperature at which thermal excitation causes molecules on its surface to gasify, leave the surface of the material, and unite into clumps of energetic submicron-size airborne particles. This process is called thermal particulation, which produces enormous numbers of submicron particles, even if the total mass of the particulated material, measured in micrograms remains the same. Thus, the slow or sudden heating of any material will cause a dramatic and rapid increase in the particle population, usually before combustion starts. That could be as early as several minutes, or as long as a week before actual fire begins in the zone being monitored.

In order to measure the number of submicron particles per cubic centimeter, the invention employs a sensitive cloud chamber as its detector. A pressure drop in the cloud chamber will cause water vapor to condense on the submicron particles in the air sample. The submicron particles per cubic centimeter (smp/cc) count measures the density of the vapor cloud, which depends upon the number of particles, not their size.

The system of the invention utilizes a Wilson Cloud Chamber together with photo-optics and microprocessor. The system responds to variations in cloud density, which are a function of the presence of the products of combustion. The device utilizes a vacuum pump to move the air samples from the area into the cloud chamber. The invention also provides electronic signals to show normal operation, malfunction, several successively higher levels of alarm, and a number that indicates the concentration of the particles being detected. The alarm threshold level is determined after an analysis of the environmental conditions at the site of installation. The invention utilizes a compact module connected to a vacuum pump and a water reservoir to create a cloud chamber, a humidity chamber to supply the cloud chamber with moisture-laden air, and passageways for collecting the air which has been sampled and subjecting it to photo-detection.

The electrical control circuits, which are operated by a microprocessor, are designed to perform a number of sampling cycles each minute, of the zone being monitored. Through the operation of humidity and vacuum valves supplying water vapor and air samples to the cloud chamber, it is possible to test samples as short as every two seconds.

It is, therefore, an object of the present invention to provide a submicron particle detector utilizing a cloud chamber and microprocessor circuitry capable of the rapid air sampling of different zones in order to detect dangerous particle accumulation.

It is another object, according to the invention, to provide a particle detector, utilizing a cloud chamber to sample air in different zones, and to establish, over a period of days, the threshold limits for the different alarm levels.

Other objects and features of the present invention will become apparent from the following detailed description considered in connection with the accompanying drawings which disclose the embodiments of the invention. It is to be understood that the drawings are designed for the purpose of illustration only, and not as a definition of the limitations of the invention.

BRIEF DESCRIPTION OF THE DRAWINGS

In the drawings wherein similar reference characters denote similar elements throughout the several views.

DETAILED DESCRIPTION OF THE INVENTION

Figure 1:
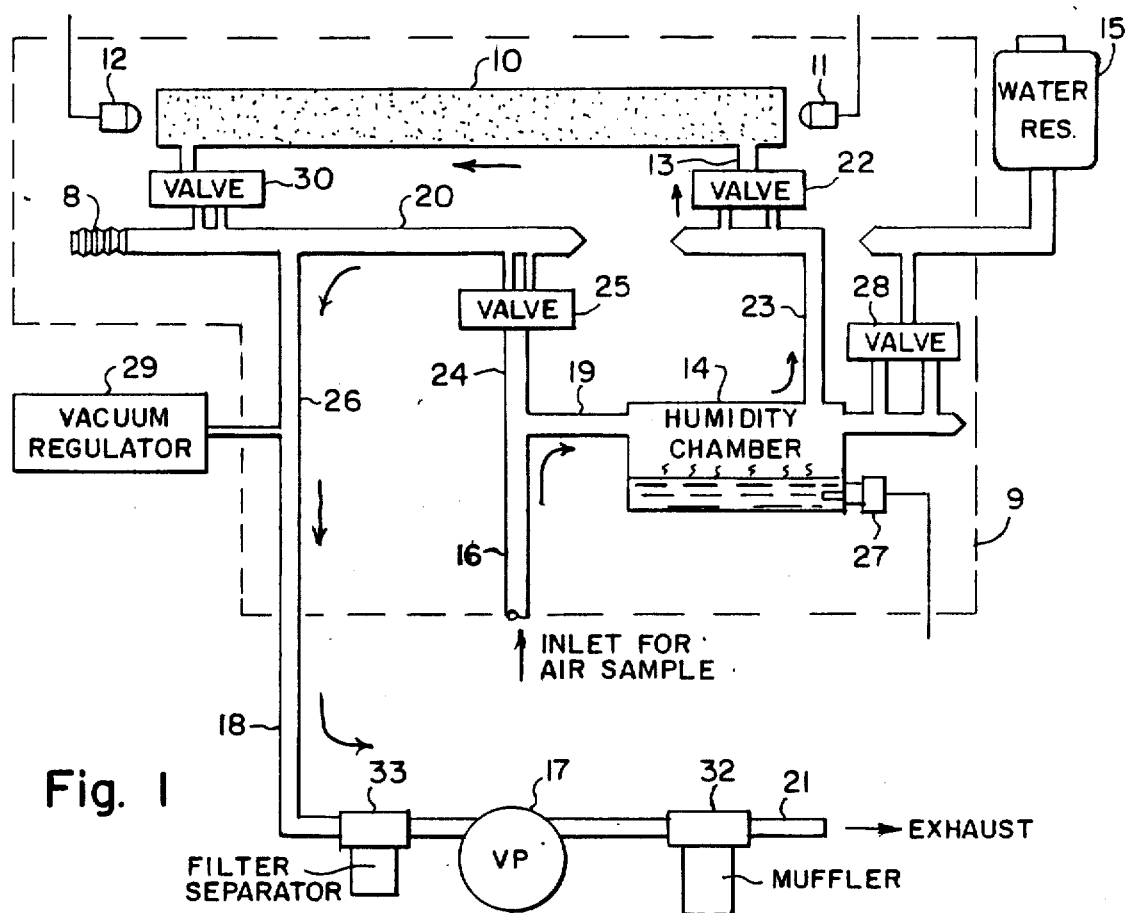
FIG. 1 is a top view of the sampling device with the system connection schematically shown.
Figure 3:
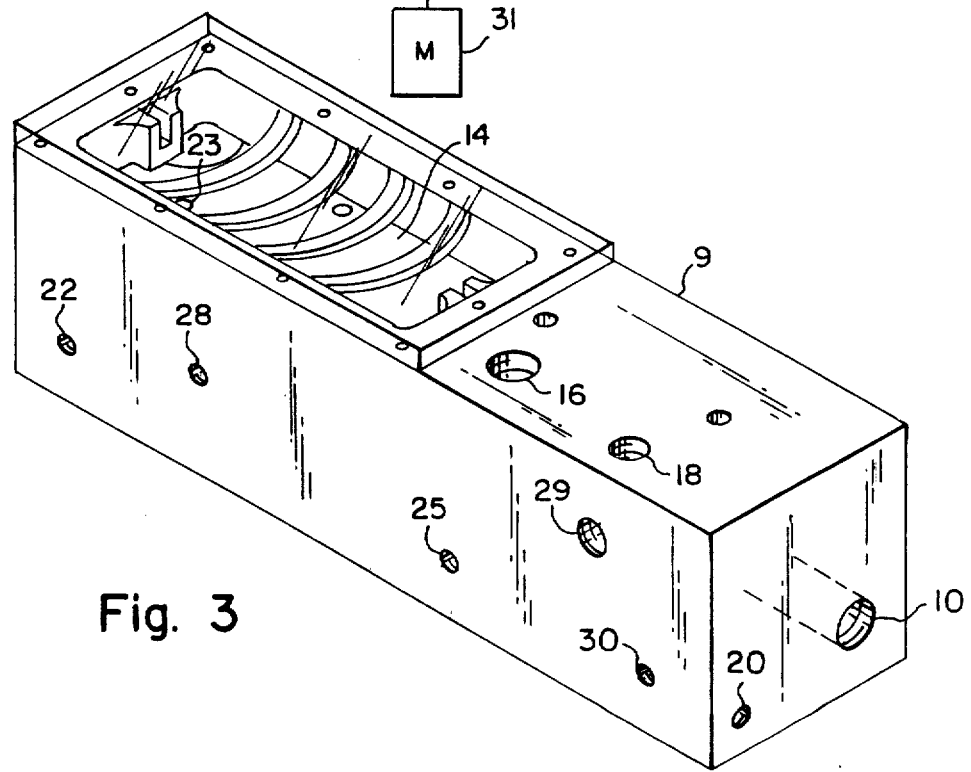
FIG. 3 is a perspective view, partly in elevation, of the sampling block, or package, containing the cloud chamber, humidity chamber, and supply passageways.
Figure 2:
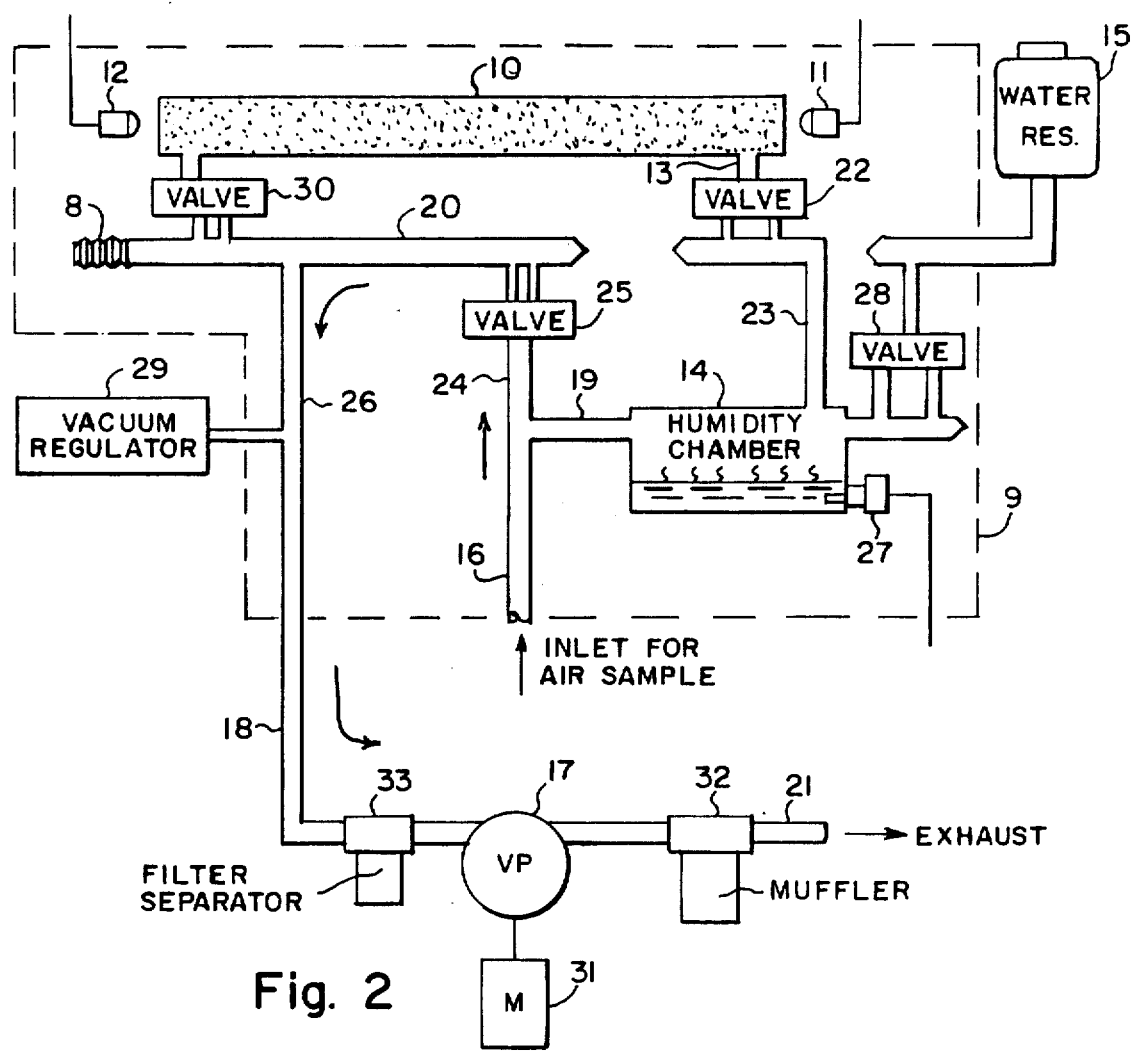
FIG. 2 is the schematic flow diagram of FIG. 1 during the sampling of air from a particular zone.

Referring now to FIGS. 1, 2, and 3, there is shown the sampling monitor device, partly in schematic form, consisting of an elongated cloud chamber 10, consisting of an elongated chamber for receiving moisture-laden air, and having optically open ends for coupling to a photo-sensitive device such as a photo transistor 12, and a source of illumination 11, such as an LED. There is also provided a humidity chamber 14, containing a level of water at the bottom of the humidity chamber that is controlled by a water level sensor device 27, so that a constant level of water from water reservoir 15 can be maintained by means of valve 28. Valve 28 is responsive to water level sensor 27 so that as the water in humidity chamber 14 evaporates, sensor 27 heats up, and signals valve 28 to open and allow additional water to pass from reservoir 15 into the floor of humidity chamber 14. The output of humidity chamber 14 is connected through a humidity valve 22, and through pipe 13 into the input side of cloud chamber 10. The opposite end of cloud chamber 10 is connected through vacuum valve 30 to a manifold 20, so that the cloud chamber can exhaust through valve 30 into manifold 20, down pipes 26 and 18, through a filter separator 33, and out exhaust tube 21. A pump 17 driven by motor 31, maintains a vacuum in pipes 18 and 26, and thus manifold 20, so that there will be a constant circulation of air entering pipes 16 and exhausting from pipe 21. A vacuum sensor 8 is mounted on the end of manifold 20 to sense the magnitude of the vacuum established.

Referring in detail to FIG. 1, in order to set up the system and establish initial conditions, humidity valve 22 is opened, and vacuum valve 30 is opened, and bypass valve 25 is closed, so that the direction of flow of air caused by pump 17 will flow into cloud chamber 10, through humidity chamber 14 and pipe 13 in order to fully purge the cloud chamber of the contaminants and to fill the cloud chamber with a sample of moist air close to 100% humidity. After a sufficient time to allow cloud chamber 10 to fill, vacuum valve 30 and humidity valve 22 are then closed to allow a settling time within cloud chamber 10, and a vacuum to build on the outlet side of the cloud chamber.

During the cycling of the valves, the output of vacuum sensor 8 is monitored to assure a proper valve operation. A vacuum reading which is not within tolerance will send a signal indicating an out-of-limit condition.

After a short dwell period, to allow the vacuum downstream of cloud chamber 10 to build to its maximum value, vacuum valve 30 is opened, quickly reducing the pressure in cloud chamber 10 and causing excess moisture in the resulting supersaturated air sample to begin condensing on sub-micron particles present in the sample. As in preceding portions of the cycle, the output of vacuum sensor 8 is monitored to determine if the proper valve operation is taking place. It should be noted here that the failure of vacuum sensor 8 in either a high or low output state will be detected, since it is in both states at different times in the cycle.

Immediately after vacuum valve 30 is opened, voltage at the collector of phototransistor 12, which increases with increasing cloud density, is digitized and stored in RAM 33 (see FIG. 4) every 5 milliseconds during cloud formation. After all data is recorded, bypass valve 25 is opened and vacuum valve 30 is closed, allowing air samples to once again be drawn into the device (see FIG. 2). The time elapsed from the bypass valve closure to its reopening can be as short as approximately 700 milliseconds. This cycle repeats approximately every eight seconds.

After the valve operation and the cloud formation take place, the device pauses before repeating the cycle. The length of this pause is determined by the condensation nuclei concentration and the "WARN" level, a level which is preset depending upon the areas being monitored. Concentrations of particles above the WARN level will cause the device to go into a short cycle mode, wherein it tests samples every two seconds instead of every eight seconds. The preferred normal cycle time is eight seconds. Two other present levels "ALERT" and "ALARM" are set at higher particle density threshold levels.

Vacuum pump 17, driven by motor 31, maintains a vacuum in line 18 so that samples of air can be continuously passed through pipe 16. Pipe 16 is coupled to the zone of the building being monitored. A zone or area consists of ten or so air intake ports which are all individually fed back to the monitor unit. At this point, all the air from the ten or so air intake ports are mixed and pass through pipe 16 to the humidification/cloud chamber assembly. As the length of each tube from the monitor to the air intake head varies, the air quantity has to be adjusted in the monitor system. A vacuum regulator, 29, controls and regulates the amount of vacuum in manifold 20 and pipes 18 and 26 during the cloud formation portion of the cycle. During the pause at the end of each cycle, a self test is performed by the device. The output of the LED/phototransistor-optical measuring system is evaluated and vacuum readings, recorded at various points in the cycle, are analyzed. The humidification chamber water level control circuit 27 is also monitored and the condensation nuclei concentration (CNC) number is determined and shown on the digital display of panel 45. Since there are always some submicron particles present even in "clean" air, a cloud should form and be detected by the device.

The absence of a detectable cloud will cause a software flag to be set indicating this condition. Any out-of-limit flag which persists for more than a predetermined length of time such as 3 cycles, will cause microprocessor 40 to drop out a trouble relay and light the fault light on panel 45. The normal operation light will then extinguish, and the panel display will indicate a malfunction code which may be used for diagnostic purposes.

The CNC number displayed on panel 45 is the digitized phototransistor 12 collector voltage value, and is used along with the present "WARN," "ALERT," and "ALARM" values to determine if a warning, alert or alarm condition exists. CNC numbers above present levels for a predetermined length of time (5 cycles) will cause the respective "WARN," "ALERT," or "ALARM" relays 44 to be energized, completing the annunciation circuit through the relay's contacts. The operation of the alarm relay is latched, and may only be cleared if the device is manually reset. The Warning and Alert relays will drop out when the CNC number falls below their respective preset levels.

Referring now in detail to FIG. 3, all of the passageway tubes 16, 26, 24, 19, 13, and manifold 20, cloud chamber 10, and humidity chamber 14 can be encased in rectangular shaped monolithic block 9 (shown in FIG. 1 by dotted line). In this embodiment, cloud chamber 10 consists of a drilled passageway through the bottom of the block which is supplied with moisture-laden air from humidity chamber 14, through internal passageways 13 as controlled by humidity valve 22.

Figure 4:
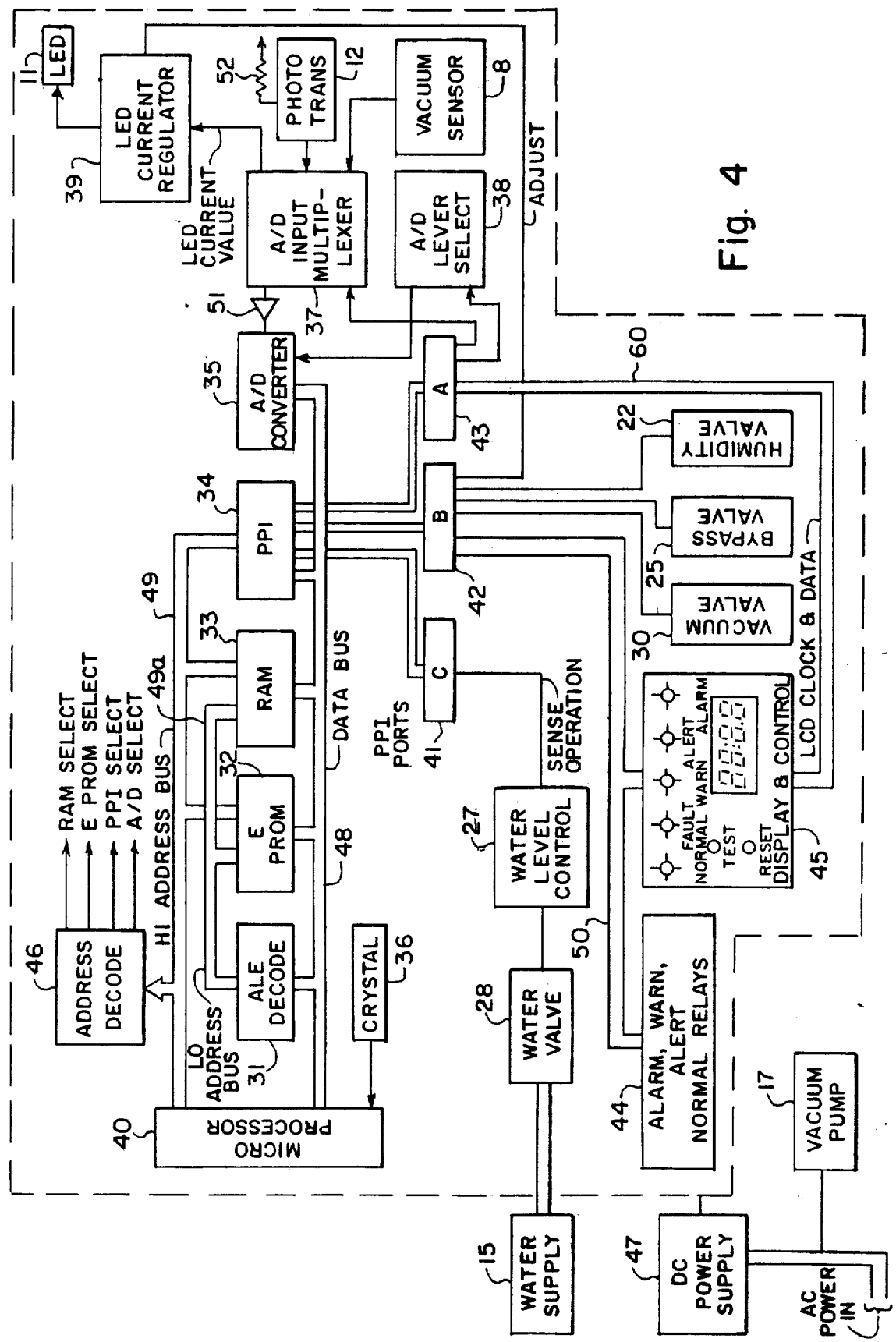
FIG. 4 is an electrical schematic diagram showing the interconnection of the components of FIGS. 1 and 2.

Referring now in more detail to FIG. 4, there is shown an electrical block diagram of the system. The system requires external DC power 47 which is used as input for all of the components shown. A microprocessor 40 is shown driven by a crystal clock 36 and has address bus 49 & 49A, and data bus 48. Coupled to these bus lines 48 and 49 are an ALE decode circuit 31, an EPROM 32, a RAM 33, and programmable peripheral interface 34 (PP1). The memory of microprocessor 40 uses an array of bistable elements. The random-access memory (RAM) 33 is a semiconductor memory which consists of an array of "gates" which may be conducting or non-conducting. Each of the memory elements is individually addressable, and each represents a single binary digit. The location where each binary digit is stored can be uniquely addressed, and it is possible to read the state of every binary digit. RAM 33 is a read-write memory wherein the binary digits within the memory can be changed as well as read by the computer.

The eraseable EPROM 32 shown coupled to RAM 33 and microprocessor 40, allows the user to program it after manufacture. Programmable peripheral interface (PP1) 34 provides the system with a plurality of I/0 lines grouped in 3 ports, 41, 42, and 43. Port A contains output lines, used to control A/D converter 35 and clock and data signals 50 for the panel display 45. Port B also contains output lines which are used to control the three air flow control solenoid valves 22, 25, and 30, and four annunciation relays 44. Port C has input lines which monitor switch positions and water level control 27. Additionally, microprocessor 40 contains input lines used to read alarm level programming dip switch 46. There is a system program which tells the present apparatus how to operate. The system program is stored in the semiconductor memory 32 so that the system program can be altered. The system program is made up of a number of instructions that are in coded binary form that are understood by microprocessor 40 so that the program can tell the microprocessor how to manipulate bits and which address lines to strobe in order to perform the required function. With instructions from the program contained in the EPROM 32, microprocessor 40 enables the various sensors and data gathering points to feed the data through interface circuitry such as the A/D converter 35 into the microprocessor 40. The data is processed by the microprocessor and stored sequentially in memory in RAM 33.

Microprocessor 40 is programmed through EPROM 32 to perform the following functions:

1. Humidity valve 22 and vacuum valve 30 open, bypass valve 25 closes to initialize the system after receiving a signal via bus 49, through PPI 34 and output port B.
2. Moisture containing air samples from zones being monitored fill cloud chamber 10.
3. After brief time interval, valves 22 and 25 close.
4. A vacuum builds on outlet of chamber 10.
5. Monitor sensor 8 to sense proper vacuum condition or signal an out-of-limit condition.
6. Open valve 30 (moisture then condenses on submicron particles in air sample).
7. Sense and digitize collection voltage of phototransistor 12.
8. Store the digital data collected in step 7 in RAM 33 every 5 milliseconds during cloud formation.
9. Open bypass valve 25, and close vacuum valve 30 after data of step 8 is stored. (Air samples are again drawn into cloud chamber 10.)
10. Display data collected in step 8 on panel 45.
11. "Warn Light" goes on if data of step 8 exceeds a predetermined first level.
12. "Alert Light" goes on if data of step 8 exceeds a predetermined second level.
13. "Alarm Light" goes on if data of step 8 exceeds a predetermined third level.
14. Activate control 27 if water level in humidity chamber 14 drops below a preset level.
15. If no detectable cloud forms in chamber 10, activate fault light on panel 45, and shut system down.

Referring to FIG. 4, the A/D converter 35 is preferably an 8-bit successive approximation type with a voltage reference input which can be adjusted to allow encoding any smaller analog voltage span to the full 8 bits of resolution. Several reference voltages are available, and are generated using A/D level selector 38 which includes a resistor type voltage divider. Each output of the voltage divider is connected to a channel on 8-channel analog digital multiplexer/demultiplexer 37. The output of A/D multiplexer 37 is connected to an operational amplifier 51 which has a gain of 1 in order to provide a non-amplified "stiff" reference voltage for A/D converter 35. The voltage divider resistors are selected so that A/D level selector 38 is preferably divided by 1, 4, 8 or 16.

Each analog input is connected to a channel on A/D multiplexer/demultiplexer 37. The one channel is used for digitizing the collector voltage of photo transistor 12 and the output of vacuum sensor 8 and the LED drive current 11.

LED 11 and phototransistor 12, used to measure cloud density, are located in the humification and cloud chamber assembly of FIG. 3. The devices are matched for operation in preferably the 990 nanometer infrared portion of the frequency spectrum. The sensitivity of phototransistor 12 is set with a fixed resistor 52. The current to LED 11 is limited to less than 10% of its nominal value in order to provide a stable output as the device ages. In addition, the current of LED 11 is regulated using a current regulator 39. Regulator 39 is a voltage-controlled current source for LED 11.

With LED regulator 39 "closed," the collector voltage of phototransistor 12 is regulated closely to a preferred reference voltage. Prior to cloud detection, regulator 39 is "opened," breaking the control loop and maintaining a predetermined current to LED 11. The phototransistor collector voltage then varies proportionally with cloud density. Vacuum sensor circuit 8 preferably uses a solid state temperature compensated resistance bridge-sensing element.

The water level control circuit 27 incorporates a negative temperature coefficient thermistor located in humidification chamber 14 and operates in a self-heating mode. When the thermistor is submerged, its internal resistance increases as it is cooled, causing an increase in voltage to eventually close water control solenoid valve 28, stopping water flow to humidification chamber 14. As chamber 14 empties, the thermistor, no longer submerged, begins to heat, causing its resistance to decrease. This decrease in resistance opens the water control solenoid valve 28 and replenishes chamber 14 with water from supply 15. Distilled water is preferably used to fill supply 15.

While only a few embodiments have been shown and described, it is to be understood that many changes and modifications may be made therewith without departing from the spirit and scope of the invention.

What is claimed is:

1. An apparatus for sampling a sample of the gaseous medium of a zone or area to determine the concentration, or changes in concentration, of small particles suspended in the gaseous medium of that area or zone comprising:
   an elongated cloud chamber having input and output openings for receiving the gaseous medium;
   a source of light disposed within said chamber;
   an optically photosensitive element disposed in said chamber and spaced-apart from said light source, said element being electronically responsive to varying levels of said light, said light source and photosensitive element being optically aligned with each other;
   an input valve coupled to said chamber input opening;
   an exhaust valve coupled to said chamber output opening;
   a microprocessor for processing data;
   a programmable memory means coupled to said microprocessor, having pre-programmed data on particle concentration levels, for sequencing said microprocessor to operate said valves sequentially to sample the gaseous medium, said memory means being coupled to said exhaust valve for opening said exhaust valve to reduce the gas pressure in said chamber to create a condition of reduced gas pressure therein, and then closing said exhaust valve to retain said condition of reduced gas pressure therein;
   said memory means being coupled to said input valve for actuating said input valve and means for
   combining a gaseous substance that becomes cloudy in the presence of the reduced gas pressure in the cloud chamber to form a cloud with the sample of gaseous medium containing small particles so that said particles precipitate or condense a portion of the cloud of said chamber in proportion to the concentration of said particles;
   means for measuring the output of said photosensitive element that measures the change in light intensity due to the effect of the concentration of particles on the light level in said chamber, said measuring means being coupled to said memory means for providing a signal proportional to the particle concentration levels in the cloud chamber;
   said memory means opening said input and output valves of said chamber to exhaust the gas and particles in said chamber so that the cycle of particle concentration measurement may be repeated;
   data storage means coupled to said memory means for recording for each cycle of operation, each of the particle concentration levels sensed and measured by said measuring means, the levels senses over several cycles of operation, and comparing the sensed and recorded particle concentration levels with the preset threshold levels; and, whereby the speed of the sampling cycle is increased by said programmable memory means when the sensed and recorded particle concentration level exceeds the preset threshold level, in order to detect the increase in particle concentration levels.
   display and control means coupled to said data storage means for providing a signal when the sensed and recorded particle concentration levels exceed the present threshold levels.

2. The apparatus as recited in claim 1, wherein said measuring means performs a multitude of samples of particle concentration readings for each cycle of operation, and wherein said data storage means averages the multitude of sample reading of each cycle before comparing the averaged reading with the preset threshold levels.

3. The apparatus as recited in claim 1, wherein said source of light is an LED disposal at one end of said cloud chamber.

4. The apparatus as recited in claim 1, wherein said optically photosensitive element is a phototransistor.

5. The apparatus as recited in claim 2, wherein said means for combining a cloudy gaseous substance comprises a humidity chamber coupled to said input valve for providing a humidity condition to said cloud chamber.

6. The apparatus as recited in claim 5, wherein said humidity chamber includes means for controlling the amount of water provided to said humidity chamber.

7. The apparatus as recited in claim 1, additionally comprising an Alert alarm coupled to said data storage means for indicating an Alert signal at a first preset particle concentration level that has been preset in said programmable memory means.

8. The apparatus as recited in claim 1, additionally comprising a Warn alarm coupled to said data storage means for indicating a Warn signal at a second preset particle concentration level that has been preset in said programmable memory means.

9. The apparatus as recited in claim 1, additionally comprising an Alarm coupled to said data storage means for indicating an Alarm signal at a third preset particle concentration level that has been preset in said programmable memory means.

10. The apparatus as recited in claim 1, additionally comprising display means coupled to said data storage means for displaying numerically the particle concentration level that has been measured in the area or zone being sampled.

11. The apparatus as recited in claim 1, wherein said exhaust valve additionally comprises a vacuum pump, and a vacuum sensor coupled to said programmable memory means for regulating the vacuum in said elongated chamber.

12. A method for sampling the gaseous medium of a zone or area to determine the concentration, or changes in concentration, of small particles suspended in the gaseous medium of that area or zone comprising the steps of:

establishing an elongated chamber having input and output openings for receiving the gaseous medium;

providing a source of light within said chamber;

providing an optically photosensitive element in said chamber and spaced-apart from said light source, said element being electronically responsive to varying levels of said light, and optically aligning said light source and photosensitive element with each other;

coupling an input valve to said chamber input opening and an exhaust valve to said chamber output opening;

opening said exhaust valve to reduce the gas pressure in said chamber creating a condition of reduced gas pressure therein;

closing said exhaust valve to retain said condition of reduced gas pressure therein;

actuating said input valve and introducing into said chamber the combination of a gaseous substance that becomes cloudy in the presence of the low gas pressure; and the sample of gaseous medium containing small particles into said cloud chamber;

actuating said exhaust valve to reduce the gas pressure in said cloud chamber so that said particles precipitate or condense a portion of the cloud of said chamber in proportion to the concentration of said particles;

measuring the output of said photosensitive element to determine the change in light intensity due to the effect of said particles on the light level in said chamber;

connecting the output of the photosensitive element to the memory means of a microprocessor, for providing a signal proportional to the level of particle concentration in the cloud chamber;

establishing preset threshold levels in the memory means of the microprocessor for establishing the minimum permissible particle concentration levels in the area or zone;

comparing the sensed and recorded particle concentration levels from each of the areas or zones, with the preset threshold levels;

displaying the sensed and recorded particle concentration levels as they are measured for each cycle, so that if the sensed and recorded particle concentration levels exceed the preset threshold levels, an alarm or indication will be set off;

opening said input and exhaust valves of said chamber and exhausting the gas and particles in said chamber so that another cycle of particle-concentration level measurement may be performed, and, increasing the speed of the sampling cycles when the sensed and recorded particle concentration level exceeds the preset threshold level, in order to detect the increase in particle concentration levels.

13. The method as recited in claim 12, wherein said optically photosensitive element is a phototransistor.

14. The method as recited in claim 12, wherein said source of light is a light emitting diode (LED).

15. The method as recited in claim 12, wherein said step of opening said exhaust valve comprises coupling an exhaust pump to said exhaust valve to reduce the gas pressure in said chamber.

16. The method as recited in claim 12, wherein following said step of measuring the output, said method additionally comprises storing said measured data, and recording each of the particle concentration levels that are measured.

17. The method as recited in claim 16, wherein said steps of storing and recording additionally comprise providing warning lights to alert, warn, or sound an alarm, if the particle concentration reaches a first, second, or third level of concentration, respectively.

18. The method as recited in claim 17, additionally comprising the step of displaying the actual particle concentration measurement on a digital read-out.

19. The method as recited in claim 1, wherein said step of measuring comprises performing a multitude of particle concentration readings for each cycle of operation, and averaging the readings taken before they are compared with the preset readings.

20. The apparatus as recited in claim 1, wherein the gaseous substance that becomes cloudy in the cloud chamber comprises water.

* * * * *